United States Patent
Fujikawa et al.

(10) Patent No.: US 7,081,559 B2
(45) Date of Patent: Jul. 25, 2006

(54) ABSORBENT COMPOSITE SHEET AND ABSORBENT ARTICLE USING THE SAME

(75) Inventors: Michiyo Fujikawa, Kagawa (JP); Takeshi Hanajiri, Kagawa (JP)

(73) Assignee: Uni-Charm Corporation, Ehime-ken (JP)

( * ) Notice: Subject to any disclaimer, the term of this patent is extended or adjusted under 35 U.S.C. 154(b) by 175 days.

(21) Appl. No.: 10/663,432

(22) Filed: Sep. 15, 2003

(65) Prior Publication Data

US 2004/0132377 A1 Jul. 8, 2004

(30) Foreign Application Priority Data

Sep. 17, 2002 (JP) ............................. 2002-269937

(51) Int. Cl.
- *A61F 13/15* (2006.01)
- *A61F 13/20* (2006.01)
- *B32B 5/06* (2006.01)
- *D04H 5/02* (2006.01)

(52) U.S. Cl. ...................... 604/358; 604/367; 604/373; 604/374; 604/385.23; 442/271; 442/408

(58) Field of Classification Search ................ 442/272, 442/271, 274, 276, 278, 408, 394; 604/358, 604/367, 374, 373, 378, 385.08, 385.23
See application file for complete search history.

(56) References Cited

U.S. PATENT DOCUMENTS

| | | |
|---|---|---|
| 4,081,582 A | 3/1978 | Butterworth et al. |
| 4,590,114 A | 5/1986 | Holtman |
| 5,683,794 A | 11/1997 | Wadsworth et al. |
| 6,235,966 B1 | 5/2001 | Magnusson et al. |
| 6,414,216 B1 | 7/2002 | Malowaniee |
| 2002/0007169 A1 | 1/2002 | Graef et al. |

FOREIGN PATENT DOCUMENTS

| | | |
|---|---|---|
| EP | 0841 156 | 5/1998 |
| EP | 1 264 561 | 12/2002 |
| JP | 07-155595 A1 | 6/1995 |
| WO | WO 91/11162 | 8/1991 |
| WO | WO 99/63922 | 12/1999 |

*Primary Examiner*—Terrel Morris
*Assistant Examiner*—Lynda Salvatore
(74) *Attorney, Agent, or Firm*—Lowe Hauptman Berner, LLP

(57) ABSTRACT

An absorbent composite sheet is thin and has a surface to be easily situated in dry condition. The absorbent composite sheet includes at least a first layer and a second layer. The first layer placed on the side of receiving a liquid is a non-woven fabric fabricated from thermoplastic synthetic resin fibers. The second layer stacked below the first layer is a non-woven fabric fabricated by entangling cellulose type fibers and thermoplastic synthetic resin fibers. The first layer and the second layer are joined by fuse bonding synthetic resin fibers of the first layer and synthetic resin fibers of the second layer. The liquid applied on a surface of the first layer is transferred to the second layer through gaps between synthetic resin fibers of the first layer.

15 Claims, 2 Drawing Sheets

ABSORBENT COMPOSITE SHEET AND ABSORBENT ARTICLE USING THE SAME

CROSS REFERENCE TO THE RELATED APPLICATION

The present application has been filed with claiming priority based on Japanese Patent Application No. 2002-269937, filed on Sep. 17, 2002. Disclosure of the above-identified Japanese Patent Application is herein incorporated by reference.

BACKGROUND OF THE INVENTION

1. Field of the Invention

The present invention relates to an absorbent composite sheet having small thickness and providing good skin contacting feeling, and an absorbent article using the same.

2. Description of the Related Art

It is a typical structure of the conventional absorbent article, such as sanitary napkin, panty liner for absorbing lady's virginal discharge or the like, to provide a liquid absorbing layer below a liquid permeable top sheet, and a liquid blocking back sheet stacked below the liquid absorbing layer. However, since the top sheet, the liquid absorbing layer and the back sheet are formed independently of each other and the absorbent article is formed by simply stacking these components, there is inherent limitation for making the absorbent article thinner. On the other hand, during manufacturing process of the absorbent article, it is required a process step of stacking the top sheet, the liquid absorbing layer and the back sheet to necessitate extra manufacturing step to restrict reduction of cost.

On the other hand, the conventional absorbent composite sheet capable of absorbing liquid by stacking or laminating the sheets has been proposed in Japanese Unexamined Patent Publication No. Heisei 7(1995)-155595.

Such conventional absorbent composite sheet is a composite body having a first layer formed by entangling cellulose type fibers (or cellulosic fibers) to a net form core body fabricated from hydrophobic fibers and a second layer formed by entangling cellulose type fibers to a net form core body fabricated from hydrophobic fibers and calboxymethylation and cross-linking of cellulose type fibers for binding to form superabsorbent polymer sheet. The net form core bodies of the first and second layers are fuse bonded for binding the first and second layers for forming the composite body.

The absorbent composite sheet has cellulose type fibers in both of the first and second layers for providing liquid absorbing and holding capacity in both of the first and second layers. Also, by forming the second layer as superabsorbent polymer sheet, higher absorbing capacity than the first layer is provided for easily transferring liquid from the first layer to the second layer and for easily absorbing the liquid in the first layer.

However, since the absorbent composite sheet disclosed in the above-identified publication has the first layer mainly formed from hydrophilic cellulose type fibers, the first layer is situated in a condition constantly containing the liquid. Also, since both of the first layer and the second layer have liquid absorbing capacity, it is inevitable that the liquid absorbed by the second layer is wetted back to the first layer. As disclosed in the above-identified publication, the absorbent composite sheet can be used as absorbent body of the sanitary napkin or the like. However, it is difficult to take a structure to directly contact the first layer to wearer's skin.

If the first layer is placed in direct contact with the wearer's skin, the liquid remained in the first layer and the liquid wetted back from the second layer to the first layer may possibly provide wet feeling to the skin and can cause skin fit on the skin in direct contact with the first layer.

SUMMARY OF THE INVENTION

The present invention has been worked out for solving the drawbacks set forth above. It is therefore an object of the present invention to provide an absorbent composite sheet which is thin and has a surface to be easily situated in dry condition, and an absorbent article using the same.

According to one aspect of the present invention, an absorbent composite sheet comprises:

at least a first layer and a second layer, the first layer placed on the side of receiving a liquid being a non-woven fabric fabricated from thermoplastic synthetic resin fibers, the second layer stacked below the first layer being a non-woven fabric fabricated by entangling cellulose type fibers and thermoplastic synthetic resin fibers, the first layer and the second layer being joined by fuse bonding synthetic resin fibers of the first layer and synthetic resin fibers of the second layer, and the liquid applied on a surface of the first layer being transferred to the second layer through gaps between synthetic resin fibers of the first layer.

The absorbent composite sheet set forth above is formed by joining the first layer formed from only synthetic resin fibers and the second layer containing cellulose type fibers at the boundary by fuse bonding of synthetic resin fibers of the first and second layers in such a manner that the liquid applied to the surface of the first layer is transferred to the second layer by capillary effect. On the other hand, by hydrophilic force of cellulose type fibers in the second layer, the liquid can be easily sucked into the second layer from the first layer. Therefore, the liquid is mainly held in the second layer and liquid holding amount of the first layer not containing cellulose type fibers can be quite small to maintain the surface of the first layer in substantially dry condition.

For example, the second layer may contain 20 to 80% by mass of the cellulose type fibers.

When the cellulose type fibers are contained in the second layer within the range set forth above, liquid absorbing performance of the second layer can be maintained high and joining force between the first layer and the second layer can be high.

On the other hand, the surface of the first layer may be a smooth surface processed by a heating roll having smooth surface.

With the construction set forth above, since the surface of the first layer which can be easily dried, is smooth, the first layer may give dry feeling to the wearer's skin by the surface of the first layer.

On the other hand, the first layer may have a fiber density in a range of 0.05 to 0.20 $g/cm^3$ when a pressure of 4.9 kPa is applied, the second layer may have a fiber density in a range of 0.015 to 0.10 $g/cm^3$ when a pressure of 4.9 kPa is applied, and the fiber density of the first layer is higher than that of the second layer.

By providing lower fiber density for the second layer containing the cellulose type fibers than that of the first layer formed from only synthetic resin fibers, returning of the liquid held in the second layer to the first layer can be prevented even when the overall absorbent composite sheet is formed thin.

According to another aspect of the invention, an absorbent article comprises an absorbent composite sheet, with taking the surface of the first layer as a skin contacting surface, and at least a liquid blocking back sheet being provided on back surface side of the second layer.

By placing the first layer in direct contact with the wearer's skin, the absorbent article can be formed thin. Also, manufacturing process of such absorbent sheet can be simplified. Furthermore, since the portion to directly contact with the wearer's skin can be easily dried, wet feeling will never be given to the skin and skin fit can be certainly avoided.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

The present invention will be discussed hereinafter in detail in terms of the preferred embodiment of an absorbent composite sheet and an absorbent article using the same in accordance with the present invention with reference to the accompanying drawings. In the following description, numerous specific details are set forth in order to provide a thorough understanding of the present invention. It will be obvious, however, to those skilled in the art that the present invention may be practiced without these specific details. In other instance, well-known structures are not shown in detail in order to avoid unnecessary obscurity of the present invention.

Figure 1:
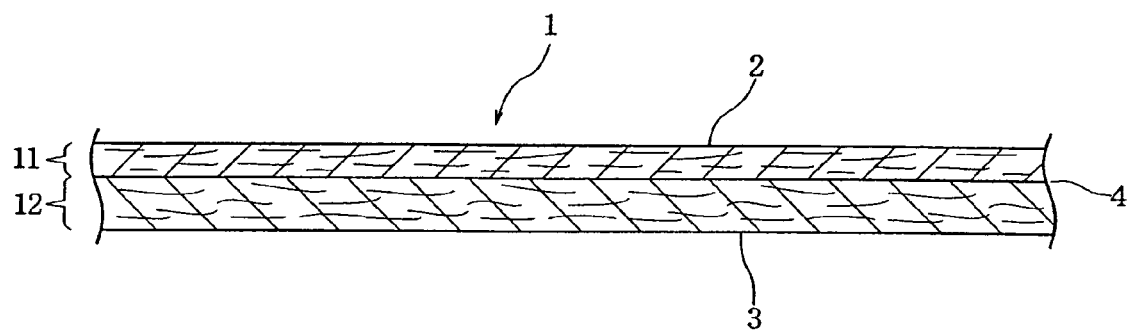
FIG. 1 is a section of the first embodiment of an absorbent composite sheet according to the present invention.
Figure 2:
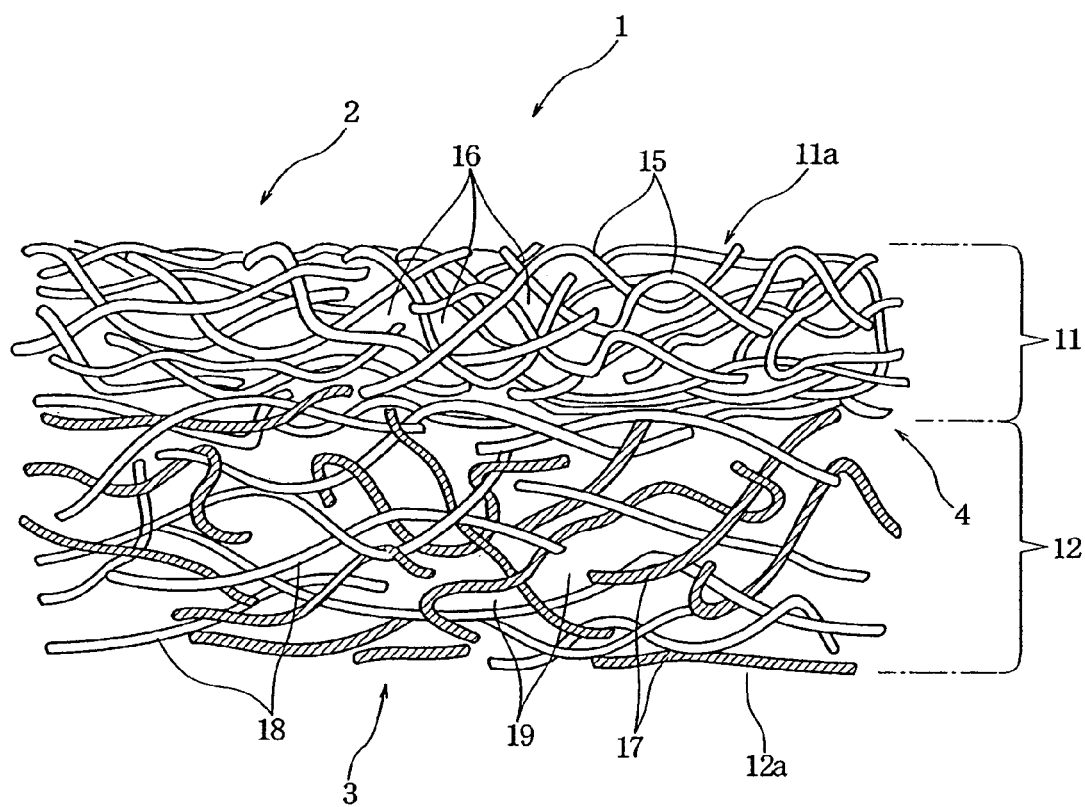
FIG. 2 is an enlarged section diagrammatically showing an internal structure of the absorbent composite sheet.

FIG. 1 is a section of the first embodiment of an absorbent composite sheet according to the present invention, and FIG. 2 is an enlarged section diagrammatically showing an internal structure of the absorbent composite sheet.

An absorbent composite sheet 1 shown in FIG. 1 is formed by joining or laminating a first layer 11 and a second layer 12 across a boundary 4. In the absorbent composite sheet 1, a surface 11a of the first layer 11 serves as a liquid receiving surface 2, and a surface 12a of the second layer 12 is a back surface 3.

As shown in FIG. 2, the first layer 11 is formed from only thermoplastic synthetic resin fibers 15. The synthetic resin fibers 15 are fuse bonded (or heat-fused) with each other to be formed into a sheet. Between adjacent synthetic resin fibers 15, gaps 16 are formed for passing the liquid therethrough. The first layer 11 serves as a liquid permeable layer passing the liquid applied on the liquid receiving surface 2 to the second layer 12.

The second layer 12 contains cellulose type fibers 17 as hydrophilic fibers and thermoplastic synthetic resin fibers 18. The cellulose type fibers 17 and the synthetic resin fibers 18 are entangled each other to be formed into a sheet. Between the cellulose type fibers 17 and the synthetic resin fibers 18, liquid holding spaces 19 are defined. The second layer 12 can serve as a liquid absorbing and holding layer.

It should be noted that, in FIG. 2, the cellulose type fibers 17 are illustrated with hatching for facilitating visual distinction of the cellulose type fibers 17 from the synthetic resin fibers 15 or the synthetic resin fibers 18 for the purpose of illustration. Actually, the cellulose type fibers 17 are white in color. The synthetic resin fibers 15 and the synthetic resin fibers 18 may also be provided white color in external appearance by admixing inorganic filler, such as titanium oxide or the like to synthetic resin forming the fibers. In the alternative, it is also possible to provide a color other than white for at least one of the synthetic resin fibers 15 and the synthetic resin fibers 18 by blending a coloring agent in the synthetic resin forming the fibers. For example, it is possible to color the synthetic resin fibers 15 of the first layer 11 in blue color and the synthetic resin fibers 18 of the second layer 12 in white color to easily distinguish the first layer 11 and the second layer 12.

At the boundary 4 between the first layer 11 and the second layer 12, the synthetic resin fibers 15 of the first layer 11 and the synthetic resin fibers 18 of the second layer 12 are fuse bonded. By this fuse bonding, the first layer 11 and the second layer 12 are joined at the boundary 4. Thus, the absorbent composite sheet 1 can be handled as substantially one sheet.

After preliminarily forming the first layer 11 and the second layer 12 into sheet shape, respectively, both layers are stacked and the synthetic resin fibers are fuse bonded at the boundary 4. Therefore, little amount of the cellulose type fibers 17 in the second layer 12 penetrate into the first layer 11. The most portion of inside of the first layer 11 does not contain the cellulose type fibers 17 and thus is formed from only synthetic resin fibers 15.

This absorbent composite sheet 1 is formed with the gaps 16 in the first layer 11 for passing the liquid therethrough and the synthetic resin fibers 15 and the synthetic resin fibers 18 are fuse bonded at the boundary 4. Therefore, it forms a structure to easily cause capillary effect to cause flow of the liquid from the first layer 11 to the second layer 12. Accordingly, the liquid applied to the surface of the first layer 11 is drawn into the second layer 12 by capillary effect and hydrophilic suction force of the cellulose type fibers 17 of the second layer 12 to be quickly absorbed in the second layer 12 through the first layer 11 and the boundary 4. Then, the liquid is held in the liquid holding spaces 19 of the second layer 12.

Since the first layer 11 is formed from only synthetic resin fibers 15, liquid remaining amount in the first layer 11 becomes small. Also, since the first layer 11 is formed from only synthetic resin fibers 15, the liquid held in the liquid holding spaces 19 of the second layer 12 hardly returns into the gaps 16 of the first layer 11. Therefore, wetting back from the second layer 12 to the first layer 11 is hardly caused. By providing lower fiber density for the second layer 12 containing the cellulose type fibers 17 than fiber density of the first layer 11 formed only from the synthetic resin fibers 15, the liquid held in the liquid holding spaces 19 of the second layer 12 hardly returns into the gaps 16 of the first layer 11. As set forth above, the liquid hardly resides within the first layer 11 to be maintained the surface 11a in nearly dried condition. Therefore, even when the surface 11a of the first layer 11 is placed in direct contact with excretion portion of a wearer's body, wet feeling may not be given to the wearer's body and skin fit on the skin may not be caused.

As set forth above, in order to facilitate prevention of returning of liquid from the second layer 12 to the first layer 11, fiber density of the second layer 12 (fiber density of the portion excluding fuse bonded boundary 4) is preferably in a range of 0.015 to 0.10 g/cm³ in a condition applied a pressure of 4.9 kPa. On the other hand, fiber density of the first layer 11 is higher than that of the second layer 12 and is preferably in a range of 0.05 to 0.20 g/cm³ in a condition applied a pressure of 4.9 kPa. A difference of the fiber densities of the first layer 11 and the second layer 12 is preferred to be greater than or equal to 0.05 g/cm³.

A process step of fuse bonding the synthetic resin fibers 15 of the first layer 11 and the synthetic resin fibers 18 of the second layer 12 at the boundary 4 is performed by heating the first layer 11 and the second layer 12 in stacked condition. In this process step, by abutting a heating roll having flat surface on the liquid receiving surface 2 side, the surface 11a of the first layer 11 becomes smooth surface. In this case, fiber density of the synthetic resin fibers 15 at the surface 11a becomes slightly higher to hold little amount of liquid on the surface 11a and the portion in the vicinity thereof. Thus, the surface 11a may be more easily maintained in dry condition. Therefore, when the smoothed surface 11a is placed in contact with the skin, dry feeling can be given to the wearer's skin.

The synthetic resin fiber 15 is a bicomponent synthetic fiber formed of two kinds of synthetic resin fibers having difference of melting point greater than or equal to 10° C. For example, sheath-core type bicomponent synthetic fiber consisted of core portion formed of polypropylene (PP) and sheath portion formed of polyethylene (PE) having lower melting point, sheath-core type bicomponent synthetic fiber consisted of core portion formed of polyethylene terephthalate (PET) and sheath portion formed of PE, side-by-side type bicomponent synthetic fiber of PP and PE, and side-by-side type bicomponent synthetic fiber of PET and PE may be used. In the alternative, the synthetic resin fiber may be monocomponent synthetic fiber of PE, monocomponent synthetic fiber of PP, and monocomponent synthetic fiber of PET. The synthetic resin fibers 15 of the first layer 11 may be any one kind of the synthetic fibers set forth above or mixed fibers of two or more kinds.

The first layer 11 is a non-woven fabric fabricated by fuse bonding the synthetic resin fibers 15 by thermal bonding method. For example, the first layer 11 may be a non-woven fabric formed by supplying fibrous web between a heating calender having smooth surface and a heating cylinder having emboss pattern on the surface for fuse bonding between the synthetic resin fibers 15 by point bonding method, or a non-woven fabric formed by blowing high temperature air to the synthetic resin fibers 15 for fuse bonding therebetween by through-air bonding method. In the alternative, the first layer 11 may also be a non-woven fabric fabricated by fuse bonding the synthetic resin fibers 15 formed through extrusion of molten synthetic resin by a heat calender roll in spun-bonding method, or a non-woven fabric fabricated by entangling and fuse bonding the synthetic resin fibers 15 formed through extrusion of molten synthetic resin and thinned into very thin fibers by hot air in meltblowing method. In the further alternative, the first layer may be a non-woven fabric fabricated by stacking and fuse bonding spun-bonded non-woven fabric and meltblown non-woven fabric with each other.

The synthetic resin fiber 15 preferably has fineness in a range of 1.1 to 4.4 dtex. Preferably, a basis weight of the first layer 11 is adjusted to be in a range of 10 to 30 g/m². When the fineness and the basis weight of the synthetic resin fiber 15 fall within the foregoing ranges, the gaps 16 suitable for passing the liquid through the first layer 11 can be formed.

When the basis weight is smaller than 10 g/m², a distance from the surface 11a to the boundary 4 with the second layer 12 becomes excessively short to easily return the liquid in the second layer 12 to the surface 11a of the first layer 11, when a pressure is exerted in the condition where the liquid is held in the second layer 12. On the other hand, when the basis weight is smaller than 10 g/m², the gaps 16 in the first layer 11 become excessively large to permit penetration of the cellulose type fibers 17 of the second layer 12 into the first layer 11 to possibly hold the liquid in the first layer 11. Conversely, when the basis weight of the first layer 11 is in excess of 30 g/m², the distance from the surface 11a to the boundary 4 with the second layer 12 becomes excessively large and the gaps 16 become excessively small to make the liquid applied to the surface 11a difficult to be sucked into the second layer 12.

In order to reduce residual liquid in the gaps 16 of the first layer 11, it is preferred that the synthetic resin fibers 15 are hydrophobic without providing hydrophilic treatment. However, it is also possible to provide hydrophilic treatment for the synthetic resin fibers 15 by admixing hydrophilic oil, such as surface active agent in the resin forming the synthetic resin fibers 15. In the alternative, it is also possible to apply hydrophilic oil, such as surface active agent, to the surface 11a after formation of the non-woven fabric of the first layer 11 or after formation of the absorbent composite sheet 1.

For example, when the first layer 11 is relatively thin and basis weight thereof is in a range of about 10 to 20 g/m², the liquid may be passed from the first layer 11 to the second layer 12 even if the hydrophilic oil is not used. Even when hydrophilic treatment with hydrophilic oil is not provided, residual liquid in the first layer 11 can be made little. Accordingly, when the first layer 11 is placed in direct contact with the wearer's skin, wet feeling may not be given to the wearer. On the other hand, when the first layer 11 is relatively thick and basis weight thereof is in a range of about 20 to 30 g/m², the distance from the surface 11a of the first layer 11 to the boundary 4 with the second layer 12 is large to hardly cause returning of the liquid in the second layer 12 to the surface 11a of the first layer 11 even if hydrophilic treatment with hydrophilic oil is applied. Therefore, even in the later case, the surface 11a can be maintained in nearly dried condition.

As the cellulose type fibers 17 of the second layer 12, one or a combination of two or more of wood pulp, rayon, acetate rayon, natural cellulose other than pulp, mercerized pulp, cross-linked pulp or the like may be used. On the other hand, as the synthetic resin fibers 18, one kind or a combination of two or more kinds of the fibers listed as the synthetic resin fibers 15 in the first layer 11 may be used. On the other hand, in order to maintain sufficient bulkiness of the second layer 12 to form a greater number of the liquid holding spaces 19 therein, it is preferred that fineness of the synthetic resin fibers 18 is greater than or equal to 4.4 dtex. On the other hand, an upper limit of the fineness is preferably about 8.8 dtex.

In the second layer 12, the cellulose type fibers 17 and the synthetic resin fibers 18 are uniformly mixed at a desired mixture ratio over the entire layer, and fibers are entangled with each other to form a non-woven fabric. For example, as the second layer 12, a non-woven fabric fabricated by spunlacing method applying water jet to a fibrous web, in which both fibers 17 and 18 are uniformly mixed, for entangling the fibers, or a non-woven fabric fabricated by needle punching method applying mechanical force to the fibrous web by needle for entangling the fibers may be used.

In the second layer 12, it is preferred that the cellulose type fiber 17 is contained in a range of 20 to 80% by mass and the synthetic resin fiber 18 is contained in remaining amount. If the content of the cellulose type fibers 17 is less than 20% by mass, capacity of the second layer 12 for absorbing and holding the liquid becomes too low to require substantial time for transferring the liquid applied to the surface 11a of the first layer 11 to the second layer 12. On the other hand, if the content of the cellulose type fibers 17 is in excess of 80% by mass, amount of the synthetic resin fibers 18 in the second layer 12 becomes small to unacceptably lower joining strength between the first layer 11 and the second layer 12.

The basis weight of the second layer 12 is determined depending upon required liquid holding capacity. In order to act as the layer for absorbing and holding the liquid, the basis weight of the second layer is preferably greater than or equal to 30 g/m$^2$. While the upper limit of the basis weight may not be specified, about 200 g/m$^2$ of basis weight may be provided for the second layer 12.

Next, discussion will be given for method of manufacturing the absorbent composite sheet 1.

The non-woven fabric formed from the synthetic resin fibers 15 and the non-woven fabric formed from the cellulose type fibers 17 and the synthetic resin fibers 18 are stacked. To the stack of the non-woven fabrics, heat is applied to cause fuse bonding of the synthetic resin fibers 15 and the synthetic resin fibers 18 at the boundary 4.

A method therefor uses two heating rolls having smooth surfaces. The stack of the non-woven fabrics are supplied between two heating rolls to apply heat under pressure to cause fuse bonding of the synthetic resin fibers 15 and the synthetic resin fibers 18 at the boundary 4.

In the absorbent composite sheet 1 manufactured using two heating rolls having smooth surfaces, the surface 11a of the first layer 11 can be formed smooth so that bulkiness becomes uniform in both of the first layer 11 and the second layer 12. Therefore, liquid may pass to the second layer over the entire surface of the liquid receiving surface 2.

Figure 3:
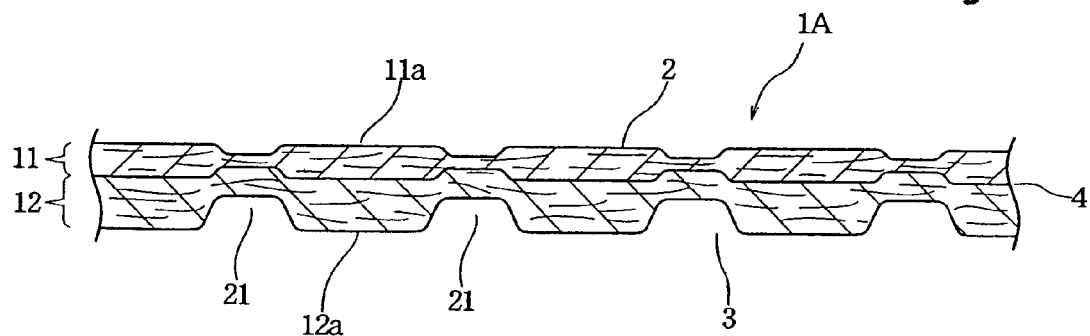
FIG. 3 is a section of the second embodiment of an absorbent composite sheet according to the present invention.
Figure 4:
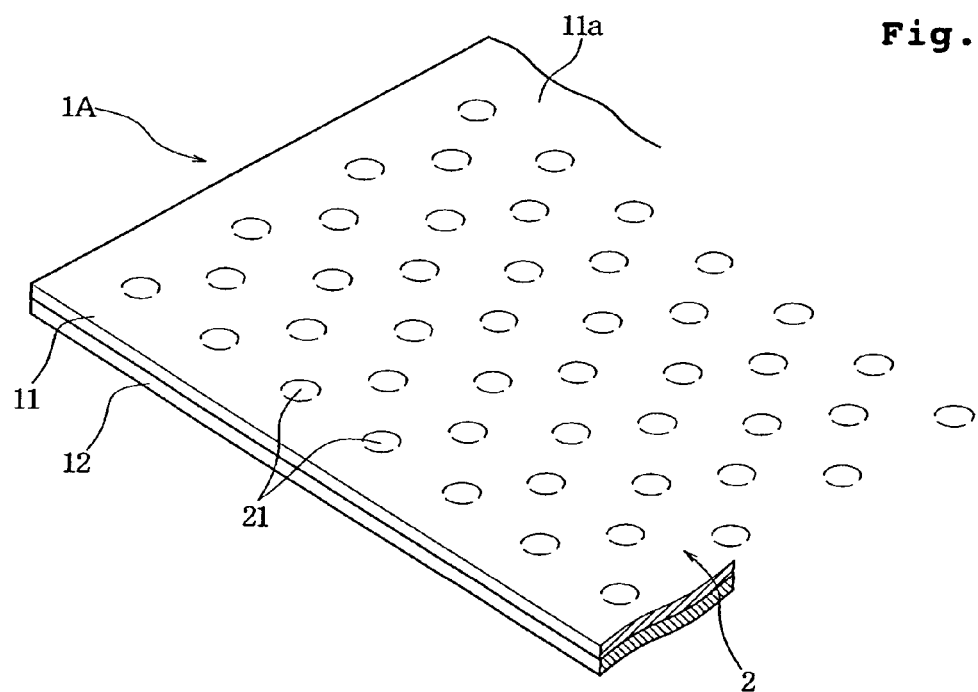
FIG. 4 is a perspective view of the second embodiment of the absorbent composite sheet.

FIG. 3 is a section of the second embodiment of an absorbent composite sheet 1A according to the present invention, and FIG. 4 is a perspective view of the second embodiment of the absorbent composite sheet 1A illustrated with directing the liquid receiving surface 2 upwardly.

The absorbent composite sheet 1A has the first layer 11 and the second layer 12 formed from the same non-woven fabrics as the first embodiment of the absorbent composite sheet 1.

The absorbent composite sheet 1A is formed by supplying the stack of two non-woven fabrics between a heating roll having smooth surface and a heating roll having emboss pattern on the surface to form dot form pressure fuse bonded portions 21 by the emboss roll (i.e., the heating roll having emboss pattern on the surface). The synthetic resin fibers 15 of the first layer 11 and the synthetic resin fibers 18 of the second layer 12 are fuse bonded at the boundary 4 at the portion of the pressure fuse bonded portions 21 as pressed by the emboss pattern.

The absorbent composite sheet 1A manufactured by the foregoing process has lower stiffness and thus becomes soft.

Furthermore, when the pressure fuse bonded portions 21 are arranged alternately both in longitudinal and lateral directions as shown in FIG. 4, the absorbent composite sheet becomes further softer.

In the absorbent composite sheet 1A, the liquid applied to the surface 11a of the first layer 11 penetrates into the first layer through portions other than the pressure fuse bonded portions 21. At this time, the liquid is drawn to the pressure fuse bonded portions 21 having higher fiber density, and is sucked into the second layer 12 across the boundary 4 at portions around the pressure fuse bonded portions 21.

In order to achieve appropriate liquid permeability and softness, it is preferred to set occupying area ratio of the pressure fuse bonded portions 21 within a range of about 5 to 40%.

Upon formation of the pressure fuse bonded portions 21, when the heating roll having smooth surface is abutted on the liquid receiving surface 2 side and the heating roll having emboss pattern is abutted on the back surface 3 side, the surface 11a of the first layer 11 can be made smooth. On the other hand, when the heating roll having smooth surface is abutted on the back surface 3 side and the heating roll having emboss pattern is abutted on the liquid receiving surface 2 side, the surface 11a of the first layer 11 can be formed with uneven emboss pattern. When the surface 11a with unevenness is contacted with the user's skin, contact area can be made small to provide better contact feeling.

As set forth above, by joining the first layer 11 and the second layer 12 by fuse bonding without using adhesive, adhesive will never appear on the surface 11a of the first layer 11 and contacting of the adhesive to the user's skin can be prevented.

Figure 5:
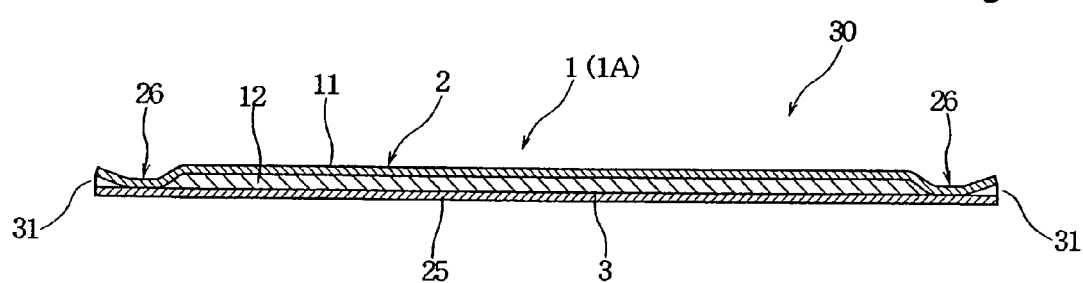
FIG. 5 is a section of one embodiment of an absorbent article according to the present invention.

FIG. 5 is a section showing a thin absorbent article 30 using the absorbent composite sheet 1 (or 1A).

The absorbent article 30 is formed by stacking a liquid blocking back sheet 25 on the back surface 3 (surface 12a of the second layer 12) of the absorbent composite sheet 1. The back sheet is formed from a moisture permeable and liquid impermeable resin film or a liquid blocking non-woven fabric.

A round seal portion 26 is formed on inside portion of a peripheral portion 31 in the condition where the absorbent composite sheet 1 and the back sheet 25 are stacked. In the round seal portion 26, the absorbent composite sheet 1 and the back sheet 25 are fuse bonded by thermo compression bonding. In the alternative, the back sheet 25 may be bonded on the back surface 3 of the absorbent composite sheet 1 by adhesive.

The absorbent article 30 is formed into an oval shape or into a shape having smaller width at the center portion in longitudinal direction and greater width at both longitudinal end portions.

The absorbent article 30 is used with directly abutting the surface 11a of the first layer 11 on the wearer's skin. Excrement liquid applied on the surface 11a of the first layer 11 is absorbed and held in the second layer 12 through the first layer 11. On the other hand, by the back sheet 25, exuding of excrement liquid toward back surface side can be prevented.

On the other hand, it may be possible to dispose another thin absorbent layer between the absorbent composite sheet 1 (or 1A) and the back sheet 25. Another absorbent layer may be formed from a pulp layer, a mixture layer of pulp and superabsorbent polymer (SAP), an air-laid non-woven fabric containing hydrophilic fibers such as pulp, stacked absorbent papers and so forth. In the alternative, it is also possible to dispose high bulkiness non-woven fabric manufactured by through-air bonding method from hydrophobic synthetic resin fibers as cushion layer between the absorbent composite sheet 1 (or 1A) and the back sheet 25.

The absorbent article 30 shown in FIG. 5 can be formed into thin as compared with the conventional absorbent article stacked with a top sheet. Also, since number of sheets to be stacked becomes small, manufacturing can be facilitated. The absorbent article 30 can be used as thin sanitary napkin, panty liner to be used for absorbing lady's virginal discharge or the like, bladder control pad for incontinence and so forth.

In the alternative, the absorbent article can be used as pet toilet mat arranged at urine discharging place of pet. In the further alternative, the absorbent composite sheet 1, 1A may be used as blood absorbing sheet for surgical operation or other medical sheet.

It should be noted that the absorbent composite sheet 1, 1A shown in FIGS. 1 and 2 is two-layer structure of the first layer 11 and the second layer 12. However, it is also possible to stack and fuse bond a sheet formed from another absorbent non-woven fabric and containing thermoplastic synthetic resin fibers, below the second layer 12, for example.

As set forth above, in the present invention, the absorbent composite sheet which is thin, demonstrates high liquid absorbing capacity, and can maintain the liquid receiving surface in nearly dried condition, can be provided. Also, the thin absorbent article having lesser number of stacks using the absorbent composite sheet, can be provided.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent article consisting essentially of an absorbent composite sheet and a liquid blocking back sheet, wherein
    said absorbent composite sheet comprises:
    a first layer on a liquid receiving side of the composite sheet and a second layer stacked below said first layer;
    said first layer being a non-woven fabric comprising thermoplastic synthetic resin fibers, said second layer being a non-woven fabric conspiring cellulose type fibers entangled with thermoplastic synthetic resin fibers;
    said first layer and said second layer being joined by fused bonds between the thermoplastic synthetic resin fibers of said first layer and the thermoplastic synthetic resin fibers of said second layer; and
    the absorbent composite sheet further comprising gaps between the thermoplastic synthetic resin fibers of said first layer for transferring a liquid from a top surface of said first layer to said second layer through said gaps;
    wherein said first layer has a fiber density in a range of 0.05 to 0.20 g/cm$^3$ when a pressure of 4.9 kPa is applied thereto, said second layer has a fiber density in a range of 0.015 to 0.10 g/cm$^3$ when a pressure of 4.9 kPa is applied thereto, and the fiber density of said first layer is higher than that of said second layer;
    said liquid blocking back sheet is disposed below said second layer; and
    said second layer defines a primary absorbent body of said absorbent article and the first layer is non-coextensive with said second layer and has a portion that extends outwardly beyond a periphery of said second layer and is bonded to the back sheet.

2. The absorbent article as set forth in claim 1, wherein said second layer contains 20 to 80% by mass of said cellulose type fibers.

3. The absorbent article as set forth in claim 1, wherein said surface of said first layer is a smooth surface processed by a heating roll having a smooth surface.

4. The absorbent article as set forth in claim 1, wherein the difference in fiber density between said first layer and said second layer is greater than or equal to 0.05 g/cm$^3$.

5. The absorbent article as set forth in claim 1, wherein the thermoplastic synthetic resin fibers of said first layer and the thermoplastic synthetic resin fibers of said second layer comprise at least a common synthetic material.

6. The absorbent article as set forth in claim 1, wherein the first layer is free of said cellulose type fibers of said second layer, except at an interface between said first and second layers.

7. The absorbent article as set forth in claim 6, wherein said composite sheet has opposite, generally planar and parallel surfaces defined by the top surface of said first layer and a bottom surface of said second layer, respectively.

8. The absorbent article as set forth in claim 6, wherein the top surface of said first layer and a bottom surface of said second layer respectively define opposite surfaces of said composite sheet, said opposite surfaces are generally planar except in embossed regions where the fused bonds between the thermoplastic synthetic resin fibers of said first and second layers are located.

9. An absorbent article comprising an absorbent composite sheet and a liquid impervious back sheet, wherein:
    said absorbent composite sheet comprises:
    a first, fibrous layer on a liquid receiving side of the composite sheet and a second, fibrous layer stacked below said first layer;
    said first layer being a first non-woven fabric comprising thermoplastic synthetic resin fibers which are hydrophobic and heat bonded together to define said first non-woven fabric;
    said second layer being a second non-woven fabric comprising hydrophilic fibers mechanically entangled with thermoplastic synthetic resin fibers;
    said first layer and said second layer being joined by fused bonds between the thermoplastic synthetic resin fibers of said first layer and the thermoplastic synthetic resin fibers of said second layer, and
    the absorbent composite sheet further comprising gaps between the thermoplastic synthetic resin fibers of said first layer for transferring a liquid from a top surface of said first layer to said second layer through said gaps;
    the first layer is free of said hydrophilic fibers of said second layer, except at an interface between said first and second layers;
    said composite sheet has opposite, generally planar and parallel surfaces defined by the top surface of said first layer and a bottom surface of said second layer, respectively;
    said liquid impervious back sheet is disposed below said second layer, wherein said second layer defines a primary absorbent body of said absorbent article and has a greatest liquid retaining capability among all components of said absorbent article; and the first layer is non-coextensive with said second layer and has a portion that extends outwardly beyond a periphery of said second layer and is bonded to the back sheet.

10. The absorbent article of claim 9, wherein a fiber density of said first layer is higher than that of said second layer.

11. The absorbent article of claim 10, wherein the thermoplastic synthetic resin fibers of said first layer has a fineness lower than that of the thermoplastic synthetic resin fibers of said second layer.

12. The absorbent article of claim 11, wherein the fineness of the thermoplastic synthetic resin fibers of said first layer is from about 1.1 to about 4.4 dtex whereas the fineness of the thermoplastic synthetic resin fibers of said second layer is from above 4.4 to about 8.8 dtex.

13. The absorbent article as set forth in claim 11, wherein the opposite surfaces of said composite sheet are generally planar except in embossed regions where the fused bonds between the thermoplastic synthetic resin fibers of said first and second layers are located.

14. The absorbent article as set forth in claim 11, wherein the thermoplastic synthetic resin fibers of said first layer and the thermoplastic synthetic resin fibers of said second layer comprise at least a common synthetic material.

15. The absorbent article as set forth in claim 9, wherein said first layer further comprises a surface active agent rendering the hydrophobic thermoplastic synthetic resin fibers of said first layer hydrophilic, and said hydrophilic fibers of said second layer are cellulosic fibers.

* * * * *